(12) United States Patent
Berg et al.

(10) Patent No.: US 7,205,314 B2
(45) Date of Patent: Apr. 17, 2007

(54) COMPOUNDS FOR THE TREATMENT OF DEMENTIA RELATED DISEASES

(75) Inventors: Stefan Berg, Södertälje (SE); Ratan Bhat, Södertälje (SE); James Empfield, Wilmington, DE (US); Sven Hellberg, Södertälje (SE); Michael Klimas, Milwaukee, WI (US); James Woods, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 91 days.

(21) Appl. No.: 10/499,217

(22) PCT Filed: Dec. 18, 2002

(86) PCT No.: PCT/SE02/02373

§ 371 (c)(1),
(2), (4) Date: Nov. 22, 2004

(87) PCT Pub. No.: WO03/053330

PCT Pub. Date: Jul. 3, 2003

(65) Prior Publication Data

US 2005/0065170 A1    Mar. 24, 2005

(30) Foreign Application Priority Data

Dec. 20, 2001   (SE)   .................... 0104340

(51) Int. Cl.
*A61K 31/47* (2006.01)
*C07D 217/16* (2006.01)

(52) U.S. Cl. .............. 514/307; 514/310; 514/301; 514/302; 514/303; 514/266.2; 546/143; 546/144; 546/114; 546/115; 546/117; 546/118; 544/283

(58) Field of Classification Search ........... 546/143, 546/144; 514/307, 310
See application file for complete search history.

(56) References Cited

FOREIGN PATENT DOCUMENTS

| EP | 1136493 A1 | 9/2001 |
|---|---|---|
| WO | WO-95/33750 A1 | 12/1995 |
| WO | WO-97/42187 A1 | 11/1997 |
| WO | WO-99/10349 A1 | 3/1999 |
| WO | WO-00/10975 A1 | 3/2000 |

OTHER PUBLICATIONS

Bruni et al. "Enolizable Cyclic Ketones. I. Reaction with Activated Heteroaromatic N-oxides" Annali di Chemica (Rome, Italy) (1967) 57(6), pp. 688-697.*

Piyasena Hewawasam et al., "Synthesis and Structure-Activity Relationships of 3-Arylosindoles: A new Class of Calcium-Dependent, Large Conductance Potassium (Maxi-K) Channel Openers with Neuroprotective Properties". J. Med. Chem., vol. 45, 2002, pp. 1487-1499.

Imahori and Uchida., Physiology and Pathology of Tau Protein Kinases in Relation to Alzheimer's Disease. J. Biochem. vol. 121, 1997, pp. 179-188.

Hoshi et al., "Regulation of mitochondrial pyruvate dehydrogenase activity by tau protein kinase I/glycogen synthase kinase 3β in brain", PNAS vol. 93, Apr. 1996, pp. 2719-2723.

Bhat et al., "Regulation and localization of tyrosine[216] phosphorylation of glycogen synthase kinase-3β in cellular and animal models of neuronal degeneration", PNAS vol. 97, No. 20, Sep. 2000, pp. 11074-11079.

Stambolic et al., "Lithium inhibits glycogen synthase kinase-3 activity and mimics wingless signalling in intact cells", Current Biol. 1996, vol. 6, pp. 1664-1668.

Klein and Melton, "A molecular mechanism for the effect of lithium on development", Proc. Natl. Acad. Sci. USA, vol. 93, Aug. 1996, pp. 8455-8459.

Kozlovaky et al., "Low GSK-3β Immunoreactivity in Postmortem Frontal Cortex of Schizophrenic Patients", Am. J. Psychiatry vol. 157(5), May 2000, pp. 831-833.

Cotter et al., Abnormalities of Wnt signalling in schizophrenia-evidence for neurodevelopmental abnormality, NeuroReport, vol. 9, May 1998, pp. 1379-1383.

Nikoulina et al., "Potential role of glycogen synthase kinase-3 in skeletal muscle insulin resistance if type 2 diabetes", Diabetes, vol. 49, Feb. 2000, pp. 263-271.

Gat et al., "De Novo Hair Follicle Morphogenesis and Hair Tumors in Mice Expressing a Truncated β-Catenin in Skin", Cell, vol. 95, Nov. 1998, pp. 605-614.

Vijajaraghavan et al., "Role for Phosphorylation of Glycogen Synthase Kinase-3α in Bovine Sperm Motility Regulation", Biol. Reprod., vol. 62(6) Jun. 2000, pp. 1647-1654.

* cited by examiner

*Primary Examiner*—Kamal S. Saeed
*Assistant Examiner*—Nyeemah Grazier
(74) *Attorney, Agent, or Firm*—George A. Gilbert

(57) ABSTRACT

The present invention relates to new compounds of formula (I) wherein Y, P, $R^1$, $R^2$, $R^3$, n, m are defined as in claim 1, a process for their preparation and new intermediates used therein, pharmaceutical composition containing said therapeutically active compounds and to the use of said active compounds in therapy, especially in the prevention and/or treatment of dementia related disease, Alzheimer's Disease and conditions associated with glycogen synthase kinase-3

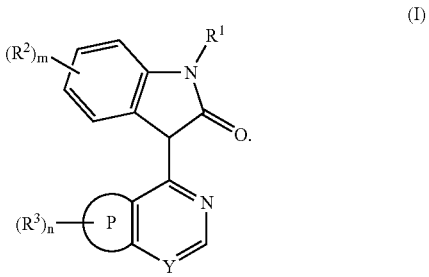

8 Claims, No Drawings

SEQUENCE LISTING

<160> NUMBER OF SEQ ID NOS: 1

<210> SEQ ID NO 1
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Biotinylated Alanine
<220> FEATURE:
<221> NAME/KEY: MOD_RES
<222> LOCATION: (11)..(11)
<223> OTHER INFORMATION: Phosphorylated Serine

<400> SEQUENCE: 1

Ala Ala Glu Glu Leu Asp Ser Arg Ala Gly Ser Pro Gln Leu
1               5                   10

COMPOUNDS FOR THE TREATMENT OF DEMENTIA RELATED DISEASES

This application is a 371 of PCT/SE02/02373, filed on Dec. 18, 2002.

FIELD OF THE INVENTION

The present invention relates to new compounds of formula I, as a free base or salts thereof, to pharmaceutical composition containing said compounds and to the use of said compounds in therapy. The present invention further relates to processes for the preparation of compounds of formula I and to new intermediates used in the preparation thereof.

BACKGROUND OF THE INVENTION

Glycogen synthase kinase 3 (GSK3) is a serine/threonine protein kinase composed of two is isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eIF2b). Insulin and growth factors activate protein kinase B, which phosphorylates GSK3 on the serine 9 residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-$\beta$ deposits. The sequence of these events in AD is unclear, but believed to be related. Glycogen synthase kinase 3$\beta$ (GSK3$\beta$) or Tau ($\tau$) phosphorylating kinase selectively phosphorylates the microtubule associated protein $\tau$ in neurons at sites that are hyperphosphorylated in AD brains. Hyperphosphorylated protein $\tau$ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia complex of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-$\beta$ to primary hippocampal cultures results in hyperphosphorylation of $\tau$ and a paired helical filaments-like state via induction of GSK3$\beta$ activity, followed by disruption of axonal transport and neuronal death (Imahori and Uchida., J. Biochem 121:179–188, 1997). GSK3$\beta$ preferentially labels neurofibrillary tangles and has been shown to be active in pre-tangle neurons in AD brains. GSK3 protein levels are also increased by 50% in brain tissue from AD patients. Furthermore, GSK3$\beta$ phosphorylates pyruvate dehydrogenase, a key enzyme in the glycolytic pathway and prevents the conversion of pyruvate to acetyl-Co-A (Hoshi et al., PNAS 93:2719–2723, 1996). Acetyl-Co-A is critical for the synthesis of acetylcholine, a neurotransmitter with cognitive functions. Thus, GSK3$\beta$ inhibition may have beneficial effects in progression as well as the cognitive deficits associated with Alzheimer's disease and other above-referred to diseases.

Chronic and Acute Neurodegenerative Diseases.

Growth factor mediated activation of the PI3K /Akt pathway has been shown to play a key role in neuronal survival. The activation of this pathway results in GSK3$\beta$ inhibition. Recent studies (Bhat et. al., PNAS 97:11074–11079 (2000)) indicate that GSK3$\beta$ activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3$\beta$. Thus, GSK3$\beta$ inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing, that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664–1668, 1996; Klein and Melton; PNAS 93:8455–8459, 1996). Inhibition of GSK3$\beta$ may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May; 157(5):831–3) found that GSK3$\beta$ levels were 41% lower in the schizophrenic patients than in comparison subjects. This study indicates that schizophrenia involves neurodevelopmental pathology and that abnormal GSK3 regulation could play a role in schizophrenia. Furthermore, reduced $\beta$-catenin levels have been reported in patients exhibiting schizophrenia (Cotter et al., Neuroreport 9:1379–1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February; 49(2):263–71). Inhibition of GSK3 increases the activity of glycogen synthase thereby decreasing glucose levels by its conversion to glycogen. GSK3 inhibition may therefore be of therapeutic relevance in the treatment of Type I and Type II diabetes and diabetic neuropathy.

Hair Loss

GSK3 phosphorylates and degrades $\beta$-catenin. $\beta$-catenin is an effector of the pathway for keratonin synthesis. $\beta$-catenin stabilisation may be lead to increase hair development. Mice expressing a stabilised $\beta$-catenin by mutation of sites phosphorylated by GSK3 undergo a process resembling de novo hair morphogenesis (Gat et al., Cell 1998 Nov. 25;95 (5):605–14)). The new follicles formed sebaceous glands and dermal papilla, normally established only in embryogenesis. Thus GSK3 inhibition may offer treatment for baldness.

Oral contraceptives

Vijajaraghavan et al. (Biol Reprod 2000 June; 62 (6): 1647–54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to provide compounds having a selective inhibiting effect at GSK3 as well as having a good bioavailability.

Accordingly, the present invention provides a compound of formula I

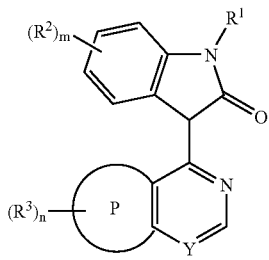

wherein:
Y is CH when P is a 5 or 6 membered aromatic, saturated or unsaturated ring containing atoms independently selected from C, N, O or S;
Y is N when P is a 5 membered aromatic or 5 or 6 membered saturated or unsaturated ring containing atoms independently selected from C, N, O or S;
$R^1$ is hydrogen;
$R^2$ is hydroxy, halogeno, fluoromethyl, difluoromethyl, trifluoromethyl, fluoromethoxy, difluoromethoxy, trifluoromethoxy, cyano, amino, nitro, $C_{1-3}$alkyl, $C_{1-3}$alkoxy, $C_{1-3}$alkanoyloxy, $C_{2-4}$alkanoyl, $C_{1-4}$-alkanoylamino, $C_{1-4}$alkoxycarbonyl, $C_{1-4}$alkylthio, $C_{1-4}$alkylsulphinyl, $C_{1-4}$alkylsulphonyl, carbamoyl, $N-C_{1-4}$alkylcarbamoyl, N,N-di($C_{1-4}$alkyl)carbamoyl, aminosulphonyl, $N-C_{1-4}$alkylaminosulphonyl, N,N-di($C_{1-4}$alkyl)aminosulphonyl, $C_{1-4}$alkylsulphonylamino, or a group $R^4X^1$, (wherin wherein $X^1$ is a direct bond, $C_{2-4}$alkanoyl, $CONR^5R^6$, $SO_2NR^7R^8$ or $SO_2R^9$ $R^5$ and $R^7$ each independently are hydrogen or $C_{1-2}$alkyl and $R^6$, $R^8$ and $R^9$ each independently are $C_{1-4}$alkyl and wherein $R^4$ is linked to $R^6$, $R^8$ or $R^9$); and
  $R^4$ is phenyl or a 5 or 6 membered heterocyclic group with one or two heteroatoms, selected independently from O, S and N, which heterocyclic group may be saturated or unsaturated and which phenyl or heterocyclic group may be substituted with one or two substituents selected independently from hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl;
$R^3$ is hydroxy, halogeno, nitro, fluoromethyl, difluoromethyl, trifluoromethyl, fluoromethoxy, difluoromethoxy, trifluoromethoxy, $C_{1-3}$alkyl, cyano, amino or $R^{10}X^2$, wherein $x^2$ is O, $CH_2$, S, SO, $SO_2$, $NR^{11}CO$, $CONR^{12}$, $SO_2NR^{13}$, $NR^{14}SO_2$ or $NR^{15}$ (wherein $R^{11}$, $R^{12}$, $R^{13}$, $R^{14}$ and $R^{15}$ each independently are hydrogen, $C_{1-3}$alkyl or $C_{1-3}$alkoxy$C_{2-3}$alkyl), or $X^2$ is a direct bond; and
$R^{10}$ is selected from one of the following groups:
1) hydrogen or $C_{1-5}$alkyl which may be substituted with one or more groups selected independently from hydroxy, fluoro and amino;
2) $C_{1-5}$alkyl$X^3COR^{16}$ (wherein $X^3$ is O or $NR^{17}$ (wherein $R^{17}$ is hydrogen, $C_{1-3}$alkyl or $C_{1-3}$alkoxy$C_{2-3}$alkyl) and $R^{16}$ is $C_{1-3}$alkyl, $NR^{18}R^{19}$ or $OR^{20}$ (wherein $R^{18}$, $R^{19}$ and $R^{20}$ each independently are hydrogen, $C_{1-3}$alkyl or $C_{1-3}$alkoxy$C_{2-3}$alkyl));
3) $C_{1-5}$alkyl$X^4R^{21}$ (wherein $X^4$ is O, S, SO, $SO_2$, OCO, $NR^{22}CO$, $CONR^{23}$, $SO_2NR^{24}$, $NR^{25}SO_2$ or $NR^{26}$ (wherein $R^{22}$, $R^{23}$, $R^{24}$, $R^{25}$ and $R^{26}$ each independently are hydrogen, $C_{1-3}$alkyl or $C_{1-3}$alkoxy$C_{2-3}$alkyl) and $R^{21}$ is hydrogen, $C_{1-3}$alkyl, cyclopentyl, cyclohexyl or a 5 or 6 membered saturated heterocyclic group with one or two heteroatoms selected independently from O, S and N, which $C_{1-3}$alkyl group may be substituted with one or two substituents selected independently from oxo, hydroxy, halogeno and $C_{1-4}$alkoxy and which heterocyclic group may be substituted with one or two substituents selected independently from oxo, hydroxy, halogeno, $C_{1-4}$alkyl, $C_{1-4}$hydroxyalkyl and $C_{1-4}$alkoxy);
4) $C_{1-5}$alkyl$X^5C_{1-5}$alkyl$X^6R^{27}$ (wherein $X^5$ and $X^6$ each independently are O, S, SO, $SO_2$, $NR^{28}CO$, $CONR^{29}$, $SO_2NR^{30}$, $NR^{31}SO_2$ or $NR^{32}$ (wherein $R^{28}$, $R^{29}$, $R^{30}$, $R^{31}$ and $R^{32}$ each independently are hydrogen, $C_{1-3}$alkyl or $C_{1-3}$alkoxy$C_{2-3}$alkyl) and $R^{27}$ is hydrogen or $C_{1-3}$alkyl);
5) $C_{1-5}$alkyl$R^{33}$ (wherein $R^{33}$ is a 5 or 6 membered saturated heterocyclic group with one or two heteroatoms selected independently from O, S and N, which heterocyclic group may be substituted with one or two substituents selected independently from oxo, hydroxy, halogeno, $C_{1-4}$alkyl, $C_{1-4}$hydroxyalkyl and $C_{1-4}$alkoxy);
6) $C_{2-5}$alkenyl$R^{33}$ (wherein $R^{33}$ is as defined hereinbefore);
7) $C_{2-5}$alkynyl$R^{33}$ (wherein $R^{33}$ is as defined hereinbefore);
8) $R^{34}$ (wherein $R^{34}$ is a pyridone group, a phenyl group or a 5 or 6 membered aromatic heterocyclic group with 1 to 3 heteroatoms selected independently from O, N and S, which pyridone, phenyl or heterocyclic group may carry up to 5 substituents selected independently from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $CONR^{35}R^{36}$ and $NR^{37}COR^{38}$ (wherein $R^{35}$, $R^{36}$, $R^{37}$ and $R^{38}$ each independently are hydrogen, $C_{1-4}$alkyl or $C_{1-3}$alkoxy$C_{2-3}$alkyl));
9) $C_{1-5}$alkyl$R^{34}$ (wherein $R^{34}$ is as defined hereinbefore);
10) $C_{2-5}$alkenyl$R^{34}$ (wherein $R^{34}$ is as defined hereinbefore);
11) $C_{2-5}$alkynyl$R^{34}$ (wherein $R^{34}$ is as defined hereinbefore);
12) $C_{1-5}$alkyl$X^7R^{34}$ (wherein $X^7$ is O, S, SO, $SO_2$, $NR^{39}CO$, $CONR^{40}$, $SO_2NR^{41}$, $NR^{42}SO_2$ or $NR^{43}$ (wherein $R^{39}$, $R^{40}$, $R^{41}$, $R^{42}$ and $R^{43}$ each independently are hydrogen, $C_{1-3}$alkyl or $C_{1-3}$alkoxy$C_{2-3}$alkyl) and $R^{34}$ is as defined hereinbefore);
13) $C_{2-5}$alkenyl$X^8R^{34}$ (wherein $X^8$ is O, S, SO, $SO_2$, $NR^{44}CO$, $CONR^{45}$, $SO_2NR^{46}$, $NR^{47}SO_2$ or $NR^{48}$ (wherein $R^{44}$, $R^{45}$, $R^{46}$, $R^{47}$ and $R^{48}$ each independently are hydrogen, $C_{1-3}$alkyl or $C_{1-3}$alkoxy$C_{2-3}$alkyl) and $R^{34}$ is as defined hereinbefore);

14) $C_{2-5}$alkynyl$X^9R^{34}$ (wherein $X^9$ is O, S, SO, SO$_2$, NR$^{49}$CO, CONR$^{50}$, SO$_2$NR$^{51}$, NR$^{52}$SO$_2$ or NR$^{53}$ (wherein $R^{49}$, $R^{50}$, $R^{51}$, $R^{52}$ and $R^{53}$ each independently are hydrogen, $C_{1-3}$alkyl or $C_{1-3}$alkoxy$C_{2-3}$alkyl) and $R^{34}$ is as defined hereinbefore); and 15) $C_{1-3}$alkyl$X^{10}C_{1-3}$alkyl$R^{34}$ (wherein $X^{10}$ is O, S, SO, SO$_2$, NR$^{54}$CO, ONR$^{55}$, SO$_2$NR$^{56}$, NR$^{57}$SO$_2$ or NR$^{58}$ (wherein $R^{54}$, $R^{55}$, $R^{56}$, $R^{57}$ and $R^{58}$ each independently are hydrogen, $C_{1-3}$alkyl or $C_{1-3}$alkoxy$C_{2-3}$alkyl) and $R^{34}$ is as defined hereinbefore);

16) $R^{33}$ (wherein $R^{33}$ is as defined hereinbefore); and

17) $C_{1-3}$alkyl$X^{10}C_{1-3}$alkyl$R^{33}$ (wherein $X^{10}$ and $R^{33}$ are as defined hereinbefore));

n is 0, 1, 2, 3 or 4;

m is 0, 1, 2, 3 or 4;

as a free base or salts thereof.

One aspect of the invention relates to compounds of formula I, wherein $R^2$ is $C_{1-3}$alkyl, halogeno, cyano, nitro, carbamoyl, N—$C_{1-4}$-alkylcarbamoyl, aminosulfonyl, $C_{1-4}$alkoxycarbonyl or a group $R^4X^1$, wherein $X^1$ is CONR$^5R^6$, (wherein $R^5$ is hydrogen or $C_{1-2}$alkyl and $R^6$ is $C_{1-4}$alkyl and wherein $R^4$ is linked to $R^6$); and n is 0, 1 or 2.

Another aspect of the invention provides for compounds of formula I, wherein $R^3$ is $R^{10}X^2$, wherein $X^2$ is O; and $R^{10}$ is selected from one of the following groups:

1) hydrogen or $C_{1-5}$alkyl;

3) $C_{1-5}$alkyl$X^4R^{21}$ (wherein $X^4$ is O or NR$^{26}$ (wherein $R^{21}$ and $R^{26}$ each independently are hydrogen, $C_{1-3}$alkyl, cyclopentyl or cyclohexyl));

4) $C_{1-5}$alkyl$X^5C_{1-5}$alkyl$X^6R^{27}$ (wherein $X^5$ and $X^6$ are O and $R^{27}$ is hydrogen or $C_{1-3}$alkyl);

5) $C_{1-5}$alkyl$R^{33}$ (wherein $R^{33}$ is a 5 or 6 membered saturated heterocyclic group with one or two heteroatoms selected independently from O, S and N);

9) $C_{1-5}$alkyl$R^{34}$ (wherein $R^{34}$ is a 5 or 6 membered aromatic heterocyclic group with 1 to 3 heteroatoms selected independently from O, N and S, which heterocyclic group may carry up to 5 substituents selected independently from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, hydoxy, cyano, CONR$^{35}R^{36}$ and NR$^{37}$COR$^{38}$ (wherein $R^{35}$, $R^{36}$, $R^{37}$ and $R^{38}$ each independently are hydrogen, $C_{1-4}$alkyl or $C_{1-3}$alkoxy$C_{2-3}$alkyl));

17) $C_{1-3}$alkyl$X^{10}C_{1-3}$alkyl$R^{33}$ (wherein $X^{10}$ is O and $R^{33}$ is a 5 or 6 membered saturated heterocyclic group with one or two heteroatoms selected independently from O, S and N);

m is 0, 1 or 2.

In a further aspect of the invention the following compounds are provided:

3-[6-(2-Methoxyethoxy)isoquinolin-1-yl]-2-oxo-2,3-dihydro-1H-indole-5-carbonitrile, 3-{6-[2-(2-Methoxyethoxy)ethoxy]isoquinolin-1-yl}-2-oxo-2,3-dihydro-1H-indole-5-carbonitrile, 2-Hydroxy-3-thieno[2,3-d]pyrimidin-4-yl-l1H-indole-5-carboxylic acid methyl ester, and 2-Hydroxy-3-(5,6,7,8-tetrahydroquinazolin-4-yl)-1H-indole-5-carboxylic acid methyl ester;

as a free base or salts thereof, and

3-{6-[2-(2-Methoxyethoxy)ethoxy]isoquinolin-1-yl}-2-oxo-2,3-dihydro-1H-indole-5-carbonitrile trifluoroacetate.

Listed below are definitions of various terms used in the specification and claims to describe the present invention.

For the avoidance of doubt it is to be understood that where in this specification a group is qualified by 'hereinbefore defined' or 'defined hereinbefore' the said group encompasses the first occurring and broadest definition as well as each and all of the preferred definitions of that group.

For the avoidance of doubt it is to be understood that in this specification '$C_{1-5}$' means a carbon group having 1, 2, 3, 4 or 5 carbon atoms.

In this specification, unless stated otherwise, the term "alkyl" includes both straight and branched chain alkyl groups. $C_{1-5}$alkyl may be methyl, ethyl, n-propyl, i-propyl, n-butyl, i-butyl, s-butyl, t-butyl, n-pentyl, i-pentyl, t-pentyl, neo-pentyl.

The term "alkoxy" as used herein, unless stated otherwise includes "alkyl"O groups in which "alkyl" is as hereinbefore defined. $C_{1-5}$alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy.

The term "alkanoyl" as used herein, unless otherwise stated includes formyl and alkylC═O groups in which "alkyl" is as defined hereinbefore, for example $C_2$alkanoyl is ethanoyl and refers to CH$_3$C═O, $C_1$alkanoyl is formyl and refers to CHO.

In this specification, unless stated otherwise, the term "alkenyl" includes both straight and branched chain alkenyl groups but references to individual alkenyl groups such as 2-butenyl are specific for the straight chain version only. Unless otherwise stated, the term "alkenyl" advantageously refers to chains with 2 to 5 carbon atoms, preferably 3 to 4 carbon atoms.

In this specification, unless stated otherwise, the term "alkynyl" includes both straight and branched chain alkynyl groups but references to individual alkynyl groups such as 2-butynyl are specific for the straight chain version only. Unless otherwise stated, the term "alkynyl" advantageously refers to chains with 2 to 5 carbon atoms, preferably 3 to 4 carbon atoms.

In this specification, unless stated otherwise, the term "5 or 6 membered aromatic, saturated or unsaturated ring containing atoms independently selected from C, N, O or S" may be, but are not limited to, furyl), isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, morpholinyl, piperazinyl, piperidyl, piperidonyl, pyrazolidinyl, pyrazolinyl, pyrrolidinyl, pyrrolinyl, thiophenyl, tetrahydropyranyl, thiomorpholinyl, cyclohexyl or cyclopentyl.

In this specification, unless stated otherwise, the term "5 membered aromatic or 5 or 6 membered saturated or unsaturated ring containing atoms independently selected from C, N, O or S" may be, but are not limited to, furyl, isoxazolyl, isothiazolyl, oxazolyl, imidazolidinyl, imidazolinyl, imidazolyl, morpholinyl, piperazinyl, piperidyl, piperidonyl, pyrazolidinyl, pyrazolinyl, pyrrolidinyl, pyrrolinyl, pyrrolyl, thiazolyl, thiophenyl, tetrahydropyranyl or thiomorpholinyl.

In this specification, unless stated otherwise, the term "5 or 6 membered heterocyclic group with one or two heteroatoms selected independently from O, S and N, which heterocyclic group may be saturated or unsaturated" includes both heteroaromatic rings and heterocyclic rings that are saturated. Examples of such heterocyclic groups includes, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl or thiomorpholinyl.

In this specification, unless stated otherwise, the term "5 or 6 membered saturated heterocyclic group with one or two heteroatoms selected independently from O, S and N" may be, but are not limited to, imidazolidinyl, morpholinyl, piperazinyl, piperidyl, piperidonyl, pyrazolidinyl, pyrrolidinyl, tetrahydropyranyl or thiomorpholinyl.

In this specification, unless stated otherwise, the term "5 or 6 membered aromatic heterocyclic group with 1 to 3 heteroatoms selected independently from O, N and S" may be, but are not limited to, furyl, imidazolyl, isoxazolyl, isothiazolyl, oxazolyl, pyrazinyl, triazinyl, pyrazolyl, pyridazinyl, pyridyl, pyrimidyl, pyrrolyl, thiazolyl or thienyl.

In this specification, unless stated otherwise, the term "5 or 6 membered heterocyclic ring containing 1 to 3 heteroatoms selected independently from O, N and S" may be, but are not limited to, furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl.

In this specification, unless stated otherwise, the term halogeno may be fluor, chlorine, bromine or iodine.

For the avoidance of any doubt, it is to be understood that when $X^2$ is, for example, a group of formula $NR^{11}CO$, it is the nitrogen atom bearing the $R^{11}$ group which is attached to the quinazoline ring and the carbonyl (CO) group is attached to $R^{10}$, whereas when $X^2$ is, for example, a group of formula $CONR^{12}$, it is the carbonyl group which is attached to the quinazoline ring and the nitrogen atom bearing the $R^{12}$ group is attached to $R^{10}$. A similar convention applies to the other two atoms $X^2$ linking groups such as $NR^{14}SO_2$ and $SO_2NR^{13}$. When $X^2$ is $NR^{15}$ it is the nitrogen atom bearing the $R^{15}$ group, which is linked to the quinazoline ring and to $R^{10}$. An analogous convention applies to other groups. It is further to be understood that when $X^2$ represents $NR^{15}$ and $R^{15}$ is $C_{1-3}$alkoxy$C_{2-3}$alkyl it is the $C_{2-3}$alkyl moiety, which is linked to the nitrogen atom of $X^2$ and an analogous convention applies to other groups.

For the avoidance of any doubt, it is to be understood that in a compound of formula I when $R^{10}$ is, for example, a group of formula $C_{1-5}$alkyl$X^{10}C_{1-5}$alkyl$R^{34}$, it is the terminal $C_{1-5}$alkyl moiety which is linked to $X^{10}$, similarly when $R^{10}$ is, for example, a group of formula $C_{2-5}$alkenyl$R^{34}$ it is the $C_{2-5}$alkenyl moiety which is linked to $X^2$ and an analogous convention applies to other groups.

For the avoidance of any doubt, it is to be understood that when $R^{34}$ carries a $C_{1-4}$aminoalkyl substituent it is the $C_{1-4}$alkyl moiety, which is attached to $R^{34}$ whereas when $R^{34}$ carries a $C_{1-4}$alkylamino substituent it is the amino moiety, which is attached to $R^{39}$ and an analogous convention applies to other groups.

For the avoidance of any doubt when $X^1$ is $C_{2-4}$alkanoyl it is the carbonyl moiety, which is linked to the heteroaromatic oxindole group and it is the alkyl moiety, which is linked to $R^4$ and an analogous convention applies to other groups.

The present invention relates to the use of compounds of formula I as hereinbefore defined as well as to the salts thereof. Salts for use in pharmaceutical compositions will be pharmaceutically acceptable salts, but other salts may be useful in the production of the compounds of formula I.

Both organic and inorganic acids can be employed to form non-toxic pharmaceutically acceptable acid addition salts of the compounds of this invention. In addition, a suitable pharmaceutically acceptable salt of the compounds of the invention is an alkali metal salt, an alkaline earth metal salt or a salt with an organic base.

Some compounds of formula I may have chiral centres and/or geometric isomeric centres (E- and Z-isomers), and it is to be understood that the invention encompasses all such optical, diastereoisomers and geometric isomers that possess GSK3 inhibitory activity.

It is to be understood that the present invention also relates to any and all tautomeric forms of the compounds of formula I.

Methods of Preparation

The present invention also relates to processes for preparing compounds of formula I. Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Greene, P. G. M. Wuts, Wiley-Interscience, New York, 1999.

Methods of Preparation of Intermediates

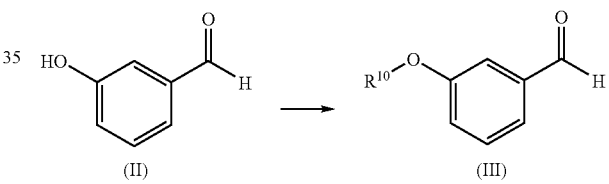

(i) Alkylation of a compound of formula II with a suitable alkylating reagent e.g. $R^{10}$—$L^1$, wherein $R^{10}$ is defined as hereinbefore and $L^1$ is a leaving group such as a halogeno e.g. bromine, chlorine or an alkane- or arenesulfonyloxy group e.g. a p-toluenesulfonyloxy group, to form a compound of formula III may be carried out in a suitable solvent such as N,N-dimethylformamide, methylene chloride or acetonitrile in the presence of a suitable base such as potassium carbonate or triethyl amine and the reaction may occur at a temperature between +20° C. and +130° C.

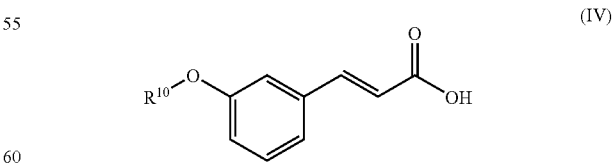

(ii) Reaction of a compound of formula III with malonic acid to form a compound of formula IV may be carried out in a suitable solvent such as pyridine or collidine, in the presence of a suitable base such as piperidine or morpholine, and the reaction may occur at a temperature between +20°

C. and +130° C., followed by the treatment with an suitable acid such as hydrochloric acid or sulfuric acid.

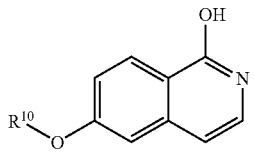

(V)

(iii) Cyclization of a compound of formula IV to a compound of formula V may be carried out by a) converting the acid function in a compound of formula IV to the corresponding acid chloride using an appropriate chlorinating reagent such as thionyl chloride or oxalyl chloride, followed by treatment with a suitable azide e.g. sodium azide in a suitable solvent such as dioxane, tetrahydrofuran, water or mixtures thereof, to form the corresponding acyl azide, followed by, b) cyclization of the acyl azide compound to the compound of formula V in a suitable solvent such as diphenyl ether, at a reaction temperature between +150° C. and +260° C.

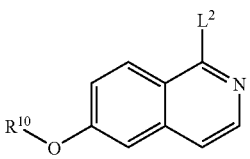

(VI)

(iv) Conversion of a compound of formula V to a compound of formula VI, wherein $L^2$ is a suitable leaving group such as a halogeno e.g. chlorine or bromine, may be carried with a suitable halogenation reagent such as thionyl chloride, oxalyl chloride, phosphoric trichloride or aluminum tribromide, in a suitable solvent such as methylene chloride, chloroform, toluene or using the halogenation reagent neat.

Methods of Preparation of End Products

Another object of the invention is a process for the preparation of compounds of general formula I and salts thereof by reacting a compound of formula VI, wherein $L^2$ is a leaving group and wherein P, Y, $R^3$ and n are as defined in general formula I, with a compound of formula VII, wherein $R^1$, $R^2$ and m are as defined in general formula I,

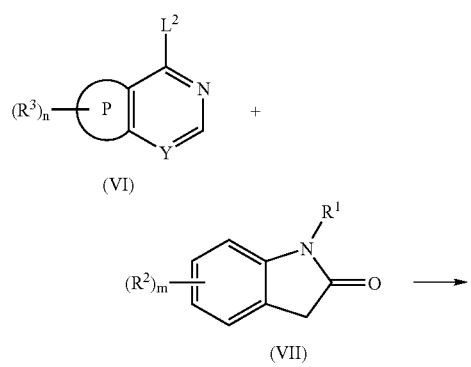

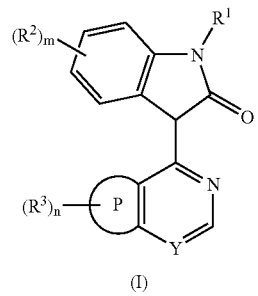

(I)

The reaction of the process may be carried out in an appropriate solvent such as an ether e.g. tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide and the reaction is conveniently effected at a temperature in the range of +10 to +150° C., preferably in the range of +20 to +90° C. The reaction is advantageously effected in the presence of a base. Such a base may be choosen from the group of organic amine bases such as pyridine, 2,6-lutidine, collidine, 4-dimethylaminopyridine, triethylamine, morpholine, N-methylmorpholine or diazabicyclo[5.4.0]undec-7-ene, tetramethylguanidine or an alkali metal or alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide.

When it is desired to obtain the acid salt, the free base may be treated with an acid using a conventional procedure.

Intermediates

The present invention further relates to new intermediates and the use of these intermediates in the preparation of compounds of formula I as defined hereinbefore.

In one aspect of the invention the intermediate is a compound of formula VI

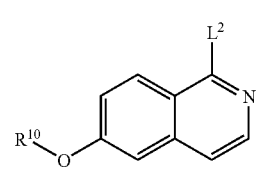

VI wherein:

$L^2$ is halogeno;

$R^{10}$ is selected from one of the following groups:

1) hydrogen or $C_{1-5}$alkyl which may be substituted with one or more groups selected independently from hydroxy, fluoro and amino;

2) $C_{1-5}$alkylX$^3$COR$^{16}$ (wherein X$^3$ is O or NR$^{17}$ (wherein R$^{17}$ is hydrogen, $C_{1-3}$alkyl or $C_{1-3}$alkoxyC$_{2-3}$alkyl) and R$^{16}$ is $C_{1-3}$alkyl, NR$^{18}$R$^{19}$ or OR$^{20}$ (wherein R$^{18}$, R$^{19}$ and R$^{20}$ each independently are hydrogen, $C_{1-3}$alkyl or $C_{1-3}$alkoxyC$_{2-3}$alkyl));

3) $C_{1-5}$alkylX$^4$R$^{21}$ (wherein X$^4$ is O, S, SO, SO$_2$, OCO, NR$^{22}$CO, CONR$^{23}$, SO$_2$NR$^{24}$, NR$^{25}$SO$_2$ or NR$^{26}$ (wherein R$^{22}$, R$^{23}$, R$^{24}$, R$^{25}$ and R$^{26}$ each independently are hydrogen, $C_{1-3}$alkyl or $C_{1-3}$alkoxy$C_{2-3}$alkyl) and R$^{21}$ is hydrogen, $C_{1-3}$alkyl, cyclopentyl, cyclohexyl or a 5 or 6 membered saturated heterocyclic group with one or two heteroatoms selected independently from O, S and N, which $C_{1-3}$alkyl group may be substituted with one or two substituents selected independently from oxo, hydroxy, halogeno and $C_{1-4}$alkoxy and which heterocyclic group may be substituted with one or two substituents selected independently from oxo, hydroxy, halogeno, $C_{1-4}$alkyl, $C_{1-4}$hydroxyalkyl and $C_{1-4}$alkoxy);

4) $C_{1-5}$alkylX$^5$$C_{1-5}$alkylX$^6$R$^{27}$ (wherein X$^5$ and X$^6$ each independently are O, S, SO, SO$_2$, NR$^{28}$CO, CONR$^{29}$, SO$_2$NR$^{30}$, NR$^{31}$SO$_2$ or NR$^{32}$ (wherein R$^{28}$, R$^{29}$, R$^{30}$, R$^{31}$ and R$^{32}$ each independently are hydrogen, $C_{1-3}$alkyl or $C_{1-3}$alkoxy$C_{2-3}$alkyl) and R$^{27}$ is hydrogen or $C_{1-3}$alkyl);

5) $C_{1-5}$alkylR$^{33}$ (wherein R$^{33}$ is a 5 or 6 membered saturated heterocyclic group with one or two heteroatoms selected independently from O, S and N, which heterocyclic group may be substituted with one or two substituents selected independently from oxo, hydroxy, halogeno, $C_{1-4}$alkyl, $C_{1-4}$hydroxyalkyl and $C_{1-4}$alkoxy);

6) $C_{2-5}$alkenylR$^{33}$ (wherein R$^{33}$ is as defined hereinbefore);

7) $C_{2-5}$alkynylR$^{33}$ (wherein R$^{33}$ is as defined hereinbefore);

8) R$^{34}$ (wherein R$^{34}$ is a pyridone group, a phenyl group or a 5 or 6 membered aromatic heterocyclic group with 1 to 3 heteroatoms selected independently from O, N and S, which pyridone, phenyl or heterocyclic group may carry up to 5 substituents selected independently from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, CONR$^{35}$R$^{36}$ and NR$^{37}$COR$^{38}$ (wherein R$^{35}$, R$^{36}$, R$^{37}$ and R$^{38}$ each independently are hydrogen, $C_{1-4}$alkyl or $C_{1-3}$alkoxy$C_{2-3}$alkyl));

9) $C_{1-5}$alkylR$^{34}$ (wherein R$^{34}$ is as defined hereinbefore);

10) $C_{2-5}$alkenylR$^{34}$ (wherein R$^{34}$ is as defined hereinbefore);

11) $C_{2-5}$alkynylR$^{34}$ (wherein R$^{34}$ is as defined hereinbefore);

12) $C_{1-5}$alkylX$^7$R$^{34}$ (wherein X$^7$ is O, S, SO, SO$_2$, NR$^{39}$CO, CONR$^{40}$, SO$_2$NR$^{41}$, NR$^{42}$SO$_2$ or NR$^{43}$ (wherein R$^{39}$, R$^{40}$, R$^{41}$, R$^{42}$ and R$^{43}$ each independently are hydrogen, $C_{1-3}$alkyl or $C_{1-3}$alkoxy$C_{2-3}$alkyl) and R$^{34}$ is as defined hereinbefore);

13) $C_{2-5}$alkenylX$^8$R$^{34}$ (wherein X$^8$ is O, S, SO, SO$_2$, NR$^{44}$CO, CONR$^{45}$, SO$_2$NR$^{46}$, NR$^{47}$SO$_2$ or NR$^{48}$ (wherein R$^{44}$, R$^{45}$, R$^{46}$, R$^{47}$ and R$^{48}$ each independently are hydrogen, $C_{1-3}$alkyl or $C_{1-3}$alkoxy$C_{2-3}$alkyl) and R$^{34}$ is as defined hereinbefore);

14) $C_{2-5}$alkynylX$^9$R$^{34}$ (wherein X$^9$ is O, S, SO, SO$_2$, NR$^{49}$CO, CONR$^{50}$, SO$_2$NR$^{51}$, NR$^{52}$SO$_2$ or NR$^{53}$ (wherein R$^{49}$, R$^{50}$, R$^{51}$, R$^{52}$ and R$^{53}$ each independently are hydrogen, $C_{1-3}$alkyl or $C_{1-3}$alkoxy$C_{2-3}$alkyl) and R$^{34}$ is as defined hereinbefore); and 15) $C_{1-3}$alkylX$^{10}$$C_{1-3}$alkylR$^{34}$ (wherein X$^{10}$ O, S, SO, SO$_2$, NR$^{54}$CO, ONR$^{55}$, SO$_2$NR$^{56}$, NR$^{57}$SO$_2$ or NR$^{58}$ (wherein R$^{54}$, R$^{55}$, R$^{56}$, R$^{57}$ and R$^{58}$ each independently are hydrogen, $C_{1-3}$alkyl or $C_{1-3}$alkoxy$C_{2-3}$alkyl) and R$^{34}$ is as defined hereinbefore);

16) R$^{33}$ (wherein R$^{33}$ is as defined hereinbefore); and

17) $C_{1-3}$alkylX$^{10}$$C_{1-3}$alkylR$^{33}$ (wherein X$^{10}$ and R$^{33}$ are as defined hereinbefore).

In another aspect of the invention the intermediate is a compound of formula VI

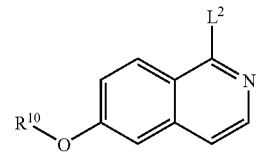

wherein:

L$^2$ is halogeno;

R$^{10}$ is selected from one of the following groups:

1) hydrogen or $C_{1-5}$alkyl;

3) $C_{1-5}$alkylX$^4$R$^{21}$ (wherein X$^4$ is O or NR$^{26}$ (wherein R$^{21}$ and R$^{26}$ each independently are hydrogen, $C_{1-3}$alkyl, cyclopentyl or cyclohexyl));

4) $C_{1-5}$alkylX$^5$$C_{1-5}$alkylX$^6$R$^{27}$ (wherein X$^5$ and X$^6$ are O and R$^{27}$ is hydrogen or $C_{1-3}$alkyl);

5) $C_{1-5}$alkylR$^{33}$ (wherein R$^{33}$ is a 5 or 6 membered saturated heterocyclic group with one or two heteroatoms selected independently from O, S and N);

9) $C_{1-5}$alkylR$^{34}$ (wherein R$^{34}$ is a 5 or 6 membered aromatic heterocyclic group with 1 to 3 heteroatoms selected independently from O, N and S, which heterocyclic group may carry up to 5 substituents selected independently from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, hydoxy, cyano, CONR$^{35}$R$^{36}$ and NR$^{37}$COR$^{38}$ (wherein R$^{35}$, R$^{36}$, R$^{37}$ and R$^{38}$ each independently are hydrogen, $C_{1-4}$alkyl or $C_{1-3}$alkoxy$C_{2-3}$alkyl));

17) $C_{1-3}$alkylX$^{10}$$C_{1-3}$alkylR$^{33}$ (wherein X$^{10}$ is O and R$^{33}$ is a 5 or 6 membered saturated heterocyclic group with one or two heteroatoms selected independently from O, S and N).

EXAMPLES

The invention will now be illustrated in the following non-limiting Examples.

Example 1

6-(2-Methoxyethoxy)isoquinolin-1-ol

To 3-(2-methoxyethoxy)benzaldehyde (7.35 g, 40.6 mmol) and pyridine (65 mL) were added malonic acid (8.5 g, 81.7 mmol) and piperidine (4 mL, 40.6 mmol). The resulting yellow solution was heated at 80° C. under nitrogen atmosphere. Gas evolved as the reaction proceeded. After 2.5 h the reaction was allowed to cool down to room temperature and stirring was continued over night. The reaction solution was concentrated in vacuo to give an oil. The oil was stirred with ice and triturated by slow addition of hydrochloric acid (12 M, 13 mL). The resulting yellow precipitate was filtered and washed with aqueous hydrochloric acid (2 M, 3×20 mL). The pale yellow solid obtained was dried in vacuo to give 8.7 g. The solid (8.7 g, 39.2 mmol) was dissolved in thionyl chloride (70 mL) and N,N-dimethylformamide (5 mL) and was refluxed under nitrogen atmosphere over night. After 16 h, the reaction solution was cooled to room temperature and concentrated in vacuo. The residue was taken up in dioxane (15 mL) and the resulting solution was added dropwise to a stirred solution of sodium azide (7.6 g, 118 mmol) in dioxane/water (26 mL, 1:1) at 5° C. The obtained suspension was stirred for 50 min at 3° C. and ethyl acetate (100 mL) was added. The layers were separated and the aqueous layer was extracted with ethyl acetate (2×75 mL). The combined organic layers were washed with water (20 mL) and brine (30 mL), dried over magnesium sulphate and filtered. Diphenyl ether (30 mL) was added and the ethyl acetate was removed in vacuo. The acyl azide solution in diphenyl ether was added during 15 min to diphenyl ether (70 mL) at 215° C. The reaction solution was refluxed 2.5 h and then stirred at room temperature over night. To the reaction solution was added diethyl ether (100 mL) and the precipitate formed was filtered off and washed with diethyl ether. The precipitate was taken up in methanol/dichloromethane, adsorbed onto silica gel (30 g) and purified by flash chromatography (gradient:dichloromethane:methanol; 98:2→95:5). The product containing fractions were combined and concentrated to give a solid. The solid was triturated with diethyl ether, filtered and dried in vacuo to give 3.15 g (37% yield) of the title compound. MS m/z 200 ($M^+$+1).

Example 2

1-Chloro-6-(2-methoxyethoxy)isoquinoline

To 6-(2-methoxyethoxy)isoquinolin-1-ol (3.15 g, 14.4 mmol) was added phosphorus trichloride (70 mL) under nitrogen atmosphere. The mixture was heated at reflux giving a nearly opaque brown solution. After 2 h at reflux, the solution was concentrated in vacuo until 20 mL remained and poured onto ice water (100 mL). The pH of the resulting mixture was adjusted to 6.5 with the addition of solid potassium carbonate and extracted with dichloromethane (3×100 mL). The combined organic layers were washed with water (50 mL) and brine (50 mL) and concentrated in vacuo. The resulting tan solid was taken up in dichloromethane, adsorbed on silica gel and purified by flash chromatography (gradient:hexane/ethyl acetate, 60:40→40: 60) to give, after drying in vacuo, 2.73 g (80% yield) of the title compound as a pale yellow solid. MS(AP+), 238 (100, $M^+$+1), 202 (33), 179 (33).

Example 3

3-[6-(2-Methoxyethoxy)isoquinolin-1-yl]-2-oxo-2,3-dihydro-1H-indole-5-carbonitrile To a solution of 5-cyanooxindole (400 mg, 2.53 mmol) in anhydrous tetrahydrofuran under nitrogen atmosphere was added N,N,N'N'-tetramethylethylenediamine (764 mL, 5.06 mmol). The solution was cooled to −71° C. and lithium diisopropylamide (3.87 mL, 5.06 mmol, 1.5 M in cyclohexane) was added slowly resulting in a vibrant yellow solution. A solution of 1-chloro-6-(2-methoxyethoxy)isoquinoline (661 mg, 2.78 mmol) in tetrahydrofuran (20 mL) was added and the reaction solution was stirred for 30 min at −7.5° C. and for 30 min at room temperature. The reaction solution was then brought to reflux. After 7.5 h, the reaction solution was cooled to room temperature and an aqueous ammonium chloride solution was added. The resulting orange solution was concentrated in vacuo. Dichloromethane was added and the red-orange precipitate formed was filtered off. The layers were separated and the aqueous layer was extracted with dichloromethane (3×100 mL). The combined organic layers were washed with water (50 mL) and brine (50 mL), dried over sodium sulphate, filtered and concentrated. The orange solid obtained was combined with the red-orange precipitate and mixed with methanol/dichloromethane. The precipitate was washed with methanol. The mother liquor was adsorbed on silica gel and purified by flash chromatography (gradient; dichloromethane/methanol, 99:1→97:3) to give 30 mg product. The flash chromatography product was combined with the precipitate and the solid was trituated with diethyl ether and dried in vacuo to give 463 mg (51% yield) of the title compound as an orange solid: mp 214–219° C. MS (AP+) m/z 360 ($M^+$+1).

Example 4

3-[2-(2-Methoxyethoxy)ethoxy]benzaldehyde

To a solution of 3-hydroxybenzaldehyde (5.0 g, 41 mmol) in N,N-dimethylformamide (100 mL) was added bromo-2-(2-methoxyethoxy)ethane (6.0 mL, 45 mmol) followed by addition of solid potassium carbonate (17 g, 122 mmol). The resulting slurry was heated under nitrogen at 57° C. for 19 h. The reaction mixture was cooled to room temperature and filtered. The filter cake was washed with methanol and the filtrate was reduced in vacuo to ~50 mL and poured into water (200 mL). The solution was acidified to pH~4 with hydrochloric acid (1 M) and extracted with ethyl acetate (3×150 mL). The combined organic layer was washed with aqueous copper sulphate (75 mL), water (100 mL) and brine (100 mL), dried over sodium sulphate, filtered and concentrated in vacuo to a viscous oil. The oil was dried in vacuo to give 9,3 g (99% yield) of the title compound as a tan oil. $^1$HNMR (300 MHz, DMSO-d6, TFA-d) δ 9.98 (s, 1H), 7.51 (m, 2H), 7.44 (s, 1H), 7.30 (m, 1H), 4.18 (t J=5 Hz, 2H), 3.76 (t, J=5 Hz, 2H), 3.60 (t, J=5 Hz, 2H), 3.46 (t, J=5 Hz, 2H), 3.25 (s, 3H).

Example 5

3-{3-[2-(2-Methoxyethoxy)ethoxy]phenyl}acrylic acid

To a solution of 3-[2-(2-methoxyethoxy)ethoxy]benzaldehyde (9.18 g, 40.9 mmol) in pyridine (70 mL) under nitrogen was added malonic acid (8.69 g, 81.9 mmol) followed by piperidine (4.13 mL, 40.9 mmol). The reaction solution was stirred for 3 h at 85° C. and left stirring over night at room temperature. The reaction solution was concentrated to an oil and left on high vacuum over night to remove the remaining pyridine. To the oil was added ice (120 g) and under vigorous stirring, concentrated hydrochloric acid (13 mL) was added. The mixture was extracted with methylene chloride (3×65 mL) and the combined organic layer was washed with water (60 mL) and brine (60 mL), dried over sodium sulphate, filtered and concentrated in vacuo. The resulting oil was dried in high vacuum to give 10.8 g (99% yield) of the title compound. $^1$HNMR (300 MHz, DMSO-d6) δ 12.28 (br s, 1H), 7.56 (d, J=16 Hz, 1H), 7.28 (m, 3H), 6.99 (dd, J=8 Hz, J=2 Hz, 1H), 6.56 (d, J=16 Hz, 1H), 4.14 (t, J=5 Hz, 2H), 3.75 (t, J=5 Hz, 2H), 3.60 (t, J=5 Hz, 2H), 3.36 (t, J=5 Hz, 2H), 3.25 (s, 3H).

Example 6

6-[2-(2-Methoxyethoxy)ethoxy]-2H-isoquinolin-1-one

To 3-{3-[2-(2-methoxyethoxy)ethoxy]phenyl}acrylic acid (10.7 g, 40.4 mmol) was added thionyl chloride (60 mL) and N,N-dimethylformamide (5 mL) and the reaction solution was refluxed under nitrogen atmosphere for 15 h. The reaction solution was dried, concentrated and the resulting oil was taken up in 1,4-dioxane (25 mL) and added dropwise during 15 min to a solution of sodium azide (7.87 g, 121 mmol) in water/dioxane (28 mL, 1:1) at 0° C. The suspension was stirred 30 min at 0° C., after which the precipitate was filtered off and washed with ethyl acetate. The filtrate was extracted with ethyl acetate (3×150 mL) and the combined organic layer was washed with water (75 mL) and brine (75 mL), dried over sodium sulphate and filtered. The azide containing solution volume was reduced in vacuo, diphenyl ether (20 mL) was added and the remaining ethyl acetate was removed in vacuo. The diphenyl ether solution of the azide was added dropwise during 20 min to hot diphenyl ether (65 mL, 230° C.) and the obtained solution was heated 2 h at reflux (~260° C.) and then left stirring at room temperature over night. Hexane was added to the reaction solution and the product precipitated out as a black oil. The oil was pre-absorbed on silica gel and purified by flash chromatography (solvent gradient:methanol/methylene chloride, 2:98→4:96) giving, after concentration and drying of the appropriate fractions, 3.4 g (32% yield) of the title compound as a yellow solid. MS (AP+) m/z 264 (M$^+$+1).

Example 7

1-Chloro-6-[2-(2-methoxyethoxy)ethoxy]isoquinoline

Phosphorus trichloride (60 mL) and 6-[2-(2-methoxyethoxy)ethoxy]-2H-isoquinolin-1-one (3.38 g, 14.3 mmol) were stirred at reflux under nitrogen atmosphere for 2 h. The reaction solution was cooled to room temperature and concentrated in vacuo until 10 mL remained. The obtained oil was poured onto ice water (80 mL) and stirred for 1 h. The mixture was neutralized with addition of solid potassium carbonate and extracted with methylene chloride (3×80 mL). The combined organic layer was washed with water (50 mL) and brine (50 mL), dried over sodium sulphate, filtered and concentrated. The obtained oil was pre-absorbed on silica gel and purified by flash chromatography (gradient:hexane/ethyl acetate, 6:4→4:6). The appropriate fractions were pooled, concentrated and dried to give 1.24 g (30% yield) of the title compound as a waxy solid. MS (AP+) m/z 282 (M+1).

Example 8

3-{6-[2-(2-Methoxyethoxy)ethoxy]isoquinolin-1-yl}-2-oxo-2,3-dihydro-1H-indole-5-carbonitrile trifluoroacetate A suspension of sodium hydride (92 mg, 3.55 mmol, 95% powder) in tetrahydrofuran (10 mL) was slowly added via a cannula to a solution of 2-oxo-5-indolinecarbonitrile (292 mg, 1.85 mmol) in tetrahydrofuran/N-methylpyrrolidinone (15 mL, 2:1) under nitrogen atmosphere. The reaction mixture was stirred at room temperature for 25 min. A solution of chloro-6-[2-(2-methoxyethoxy)ethoxy]isoquinoline (400 mg, 1.42 mmol) in tetrahydrofuran (10 mL) was added and the reaction solution was stirred at room temperature over night. The reaction was quenched by slow addition of hydrochloric acid (1 M) and concentrated in vacuo to a slurry. The slurry was diluted with acetonitrile (5 mL) and purified by prep RP-HPLC (C18 2" column, gradient:acetonitril/water, 20:80→0:100+0.1% TFA). The appropriate fractions were pooled and lyophilized giving 193 mg (27% yield) of the title compound as an orange trifluoroacetate salt. MS (AP+) m/z 404 (M+1).

Example 9

2-Hydroxy-3-thieno[2,3-d]pyrimidin-4-yl-1H-indole-5-carboxylic acid methyl ester Sodium tert-butoxide (40.3 mg, 0.42 mmol) and methyl 2-oxo-5-indolinecarboxylate (17.6 mg, 0.092 mmol) in N-methylpyrrolidinone (1 mL) under nitrogen atmosphere were stirred for 5 min at room temperature. A solution of 4-chlorothieno[2,3-d]pyrimidine (0.1 mL, 0.84 M, corresponding to 14.3 mg, 0.084 mmol) in N-methylpyrrolidinone was added and the reaction mixture was stirred at room temperature over night. The reaction mixture was diluted with water (20 mL) and acidified with hydrochloric acid (1 M) and extracted with ethyl acetate (2×15 mL). The combined organic layer was washed with brine, dried with sodium sulphate, filtered and concentrated. The crude product was triturated with methylene chloride to give 10 mg (36% yield) of the title compound as a bronze solid. MS (AP−) m/z 324 (M−1).

Example 10

2-Hydroxy-3-(5,6,7,8-tetrahydroquinazolin-4-yl)-1H-indole-5-carboxylic acid methyl ester The title compound was synthesized according to the procedure described for Example 9 using sodium tert-butoxide (48 mg, 0.5 mmol), methyl 2-oxo-5-indolinecarboxylate (21 mg, 0.11 mmol) and 4-chloro-5,6,7,8-tetrahydroquinazoline solution (0.1 mL, 1 M in N-methylpyrrolidinone, corresponding to 17 mg, 0.1 mmol; described in: Budesinsky Z., Roubinek F. Collect. Czech. Chem. Commun., 1964, 29, 2341). The crude oil was purified on SCX-column pre-rinsed with methanol using ethyl acetate, methylene chloride, methylene chloride/methanol 1:1, and methanol/ammonia (2 M, aq) as elution solvents.

The product was triturated with diethyl ether and dried in high vacuum to give 7 mg (22% yield) of the title compound as a solid. MS (AP+) m/z 324.1 (M+1).

Pharmaceutical Compositions

According to one aspect of the present invention there is provided a pharmaceutical composition comprising a compound of formula I, as a free base or salts thereof, for use in prevention and/or treatment of dementia related diseases, Alzheimer's Disease and conditions associated with glycogen synthase kinase-3 and other conditions listed below.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream or for rectal administration as a suppository.

In general the above compositions may be prepared in a conventional manner using pharmaceutically carriers or diluents.

Suitable daily doses of the compounds of formula I in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

Medical Use

Surprisingly, it has been found that the compounds defined in the present invention, as a free base or salts thereof, are useful in therapy. The compounds of the present invention are well suited for inhibiting glycogen synthase kinase-3 (GSK3). Accordingly, the compounds of the present invention are expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compounds of the invention are well suited for the prevention and/or treatment of conditions associated with glycogen synthase kinase-3 in the central and peripheral nervous system. In particular, the compounds of the invention are expected to be suitable in the manufacture of a medicament for the prevention and/or treatment of dementia related diseases and Alzheimer's Disease.

The dementia related diseases are selected from the group consisting of Frontotemporal dementia Parkinson's Type, Parkinson dementia complex of Guam, HIV dementia, diseases with associated neurofibrillar tangle pathologies, predemented states, vascular dementia, dementia with Lewy bodies, Frontotemporal dementia and dementia pugilistica. The compounds of the invention are also expected to be suitable in the manufacture of a medicament for the prevention and/or treatment of amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication.

The compounds of the invention are further expected to be suitable in the manufacture of a medicament for the prevention and/or treatment of Mild Cognitive Impairment, Age-Associated Memory Impairment, Age-Related Cognitive Decline, Cognitive Impairement No Dementia, mild cognitive decline, mild neurocognitive decline, Late-Life Forgetfulness, memory impairment and cognitive impairment and androgenetic alopecia.

The present invention relates also to the use of a compound of formula I as defined hereinbefore, in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of prevention and/or treatment of dementia related diseases, Alzheimer's Disease and conditions associated with glycogen synthase kinase-3 and other conditions listed above comprising administering to a mammal, including man, in need of such prevention and/or treatment a therapeutically effective amount of a compound of formula I, as hereinbefore defined.

Non-Medical Use

In addition to their use in therapeutic medicine, the compounds of formula I as a free base or a salts thereof, are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutics agents.

Pharmacology

Determination of ATP Competition in Scintillation Proximity GSK3β Assay.

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), (SEQ ID NO: 1), was added at a final concentration of 1 µM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 µg BSA/25 µl. The reaction was initiated by the addition of 0.04 µCi [$\gamma$-$^{33}$P]ATP (Amersham, UK) and unlabelled ATP at a final concentration of 1 µM and assay volume of 25 µl. After incubation for 20 minutes at room temperature, each reaction was terminated by the addition of 25 µl stop solution containing 5 mM EDTA, 50 µM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK30β, used to calculate the inhibition constants ($K_i$) of the various compounds, was 20 µM.

The following abbreviations have been used:

| | |
|---|---|
| ATP | Adenosine Triphophatase |
| BSA | Bovin Serum Albumin |
| EDTA | Ethylenediaminetetraacetic acid |
| GSK3 | Glycogen synthase kinase 3 |
| MOPS | Morpholinepropanesulfonic acid |
| SPA | Scintillation Proximity Assay |

RESULTS

Typical $K_i$ values for the compounds of the present invention are in the range of about 0.001 to about 10,000 nM. Other values for $K_i$ are in the range of about 0.001 to about 1000 nM. Further values for $K_i$ are in the range of about 0.001 nM to about 300 nM.

The invention claimed is:

1. A compound of formula I

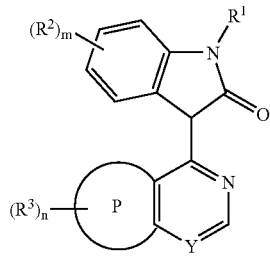

(I)

wherein:

Y is CH when P is a phenyl ring;

$R^1$ is hydrogen;

$R^2$ is hydroxy, halogeno, fluoromethyl, difluoromethyl, trifluoromethyl, fluoromethoxy, difluoromethoxy, trifluoromethoxy, cyano, amino, nitro, $C_{1-3}$alkyl, $C_{1-3}$alkoxy, $C_{1-3}$alkanoyloxy, $C_{2-4}$alkanoyl, $C_{1-4}$alkanoylamino, $C_{1-4}$alkoxycarbonyl, $C_{1-4}$alkylthio, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, $C_{1-4}$alkylsulphonylamino, or a group $R^4X^1$, wherein $X^1$ is a direct bond, $C_{2-4}$alkanoyl, $CONR^5R^6$, $SO_2NR^7R^8$ or $SO_2R^9$ (wherein $R^5$ and $R^7$ each independently are hydrogen or $C_{1-2}$alkyl and $R^6$, $R^8$ and $R^9$ each independently are $C_{1-4}$alkyl; and wherein $R^4$ is linked to $R^6$, $R^8$ or $R^9$); and $R^4$ is phenyl or a 5 or 6 membered heterocyclic group with one or two heteroatoms, selected independently from O, S and N, which heterocyclic group may be saturated or unsaturated and which phenyl or heterocyclic group may be substituted with one or two substituents selected independently from hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl;

$R^3$ is hydroxy, halogeno, nitro, fluoromethyl, difluoromethyl, trifluoromethyl, fluoromethoxy, difluoromethoxy, trifluoromethoxy, $C_{1-3}$alkyl, cyano, amino or $R^{10}X^2$, wherein $X^2$ is O, $CH_2$, S, SO, $SO_2$, $NR^{11}CO$, $CONR^{12}$, $SO_2NR^{13}$, $NR^{14}SO_2$ or $NR^{15}$ (wherein $R^{11}$, $R^{12}$, $R^{13}$, $R^{14}$ and $R^{15}$ each independently are hydrogen, $C_{1-3}$alkyl or $C_{1-3}$alkoxy$C_{2-3}$alkyl) , or $X^2$ is a direct bond; and $R^{10}$ is selected from one of the following:

1) hydrogen or $C_{1-5}$alkyl which may be substituted with one or more groups selected independently from hydroxy, fluoro and amino;

2) $C_{1-5}$alkyl$X^3COR^{16}$, (wherein $X^3$ is O or $NR^{17}$ (wherein $R^{17}$ is hydrogen, $C_{1-3}$alkyl or $C_{1-3}$alkoxy$C_{2-3}$alkyl) and $R^{16}$ is $C_{1-3}$alkyl, $NR^{18}R^{19}$ or $OR^{20}$ (wherein $R^{18}$, $R^{19}$ and $R^{20}$ each independently are hydrogen, $C_{1-3}$alkyl or $C_{1-3}$alkoxy$C_{2-3}$alkyl));

3) $C_{1-5}$alkyl$X^4R^{21}$, (wherein $X^4$ is O, S, SO, $SO_2$, OCO, $NR^{22}CO$, $CONR^{23}$, $SO_2NR^{24}$, $NR^{25}SO_2$ or $NR^{26}$ (wherein $R^{22}$, $R^{23}$, $R^{24}$, $R^{25}$ and $R^{26}$ each independently are hydrogen, $C_{1-3}$alkyl or $C_{1-3}$alkoxy$C_{2-3}$alkyl) and $R^{21}$ is hydrogen, $C_{1-3}$alkyl, cyclopentyl, cyclohexyl or a 5 or 6 membered saturated heterocyclic group with one or two heteroatoms selected independently from O, S and N, which $C_{1-3}$alkyl group may be substituted with one or two substituents selected independently from oxo, hydroxy, halogeno and $C_{1-4}$alkoxy; and which heterocyclic group may be substituted with one or two substituents selected independently from oxo, hydroxy, halogeno, $C_{1-4}$alkyl, $C_{1-4}$hydroxyalkyl and $C_{1-4}$alkoxy);

4) $C_{1-5}$alkyl$X^5C_{1-5}$alkyl$X^6R^{27}$, (wherein $X^5$ and $X^6$ each independently are O, S, SO, $SO_2$, $NR^{28}CO$, $CONR^{29}$, $SO_2NR^{30}$, $NR^{31}SO_2$ or $NR^{32}$ (wherein $R^{28}$, $R^{29}$, $R^{30}$, $R^{31}$ and $R^{32}$ each independently are hydrogen, $C_{1-3}$alkyl or $C_{1-3}$alkoxy$C_{2-3}$alkyl) and $R^{27}$ is hydrogen or $C_{1-3}$alkyl);

5) $C_{1-5}$alkyl$R^{33}$, (wherein $R^{33}$ is a 5 or 6 membered saturated heterocyclic group with one or two heteroatoms selected independently from O, S and N, which heterocyclic group may be substituted with one or two substituents selected independently from oxo, hydroxy, halogeno, $C_{1-4}$alkyl, $C_{1-4}$hydroxyalkyl and $C_{1-4}$alkoxy);

6) $C_{2-5}$alkenyl$R^{33}$, (wherein $R^{33}$ is as defined hereinbefore);

7) $C_{2-5}$alkynyl$R^{33}$, (wherein $R^{33}$ is as defined hereinbefore);

8) $R^{34}$, (wherein $R^{34}$ is a pyridone group, a phenyl group or a 5 or 6 membered aromatic heterocyclic group with 1 to 3 heteroatoms selected independently from O, N and S, which pyridone, phenyl or heterocyclic group may carry up to 5 substituents selected independently from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $CONR^{35}R^{36}$ and $NR^{37}COR^{38}$ (wherein $R^{35}$, $R^{36}$, $R^{37}$ and $R^{38}$ each independently are hydrogen, $C_{1-4}$alkyl or $C_{1-3}$alkoxy$C_{2-3}$alkyl));

9) $C_{1-5}$alkyl$R^{34}$, (wherein $R^{34}$ is as defined hereinbefore);

10) $C_{2-5}$alkenyl$R^{34}$, (wherein $R^{34}$ is as defined hereinbefore);

11) $C_{2-5}$alkynyl$R^{34}$, (wherein $R^{34}$ is as defined hereinbefore);

12) $C_{1-5}$alkyl$X^7R^{34}$, (wherein $X^7$ is O, S, SO, $SO_2$, $NR^{39}CO$, $CONR^{40}$, $SO_2NR^{42}$, $NR^{41}SO_2$ or $NR^{43}$ (wherein $R^{39}$, $R^{40}$, $R^{41}$, $R^{42}$ and $R^{43}$ each independently are hydrogen, $C_{1-3}$alkyl or $C_{1-3}$alkoxy$C_{2-3}$alkyl) and $R^{34}$ is as define hereinbefore);

13) $C_{2-5}$alkenyl$X^8R^{34}$, (wherein $X^8$ is O, S, SO, $SO_2$, $NR^{44}CO$, $CONR^{45}$, $SO_2NR^{46}$, $NR^{47}SO_2$ or $NR^{48}$ (wherein $R^{44}$, $R^{45}$, $R^{46}$, $R^{47}$ and $R^{48}$ each independently are hydrogen, $C_{1-3}$alkyl or $C_{1-3}$alkoxy$C_{2-3}$alkyl) and $R^{34}$ is as defined hereinbefore);

14) $C_{2-5}$alkynyl$X^9R^{34}$, (wherein $X^9$ is O, S, SO, $SO_2$, $NR^{49}CO$, $CONR^{50}$, $SO_2NR^{51}$, $NR^{52}SO_2$ or $NR^{53}$ (wherein $R^{49}$, $R^{50}$, $R^{51}$, $R^{52}$ and $R^{53}$ each independently are hydrogen, $C_{1-3}$alkyl or $C_{1-3}$alkoxy$C_{2-3}$alkyl and $R^{34}$ is as defined hereinbefore); and 15) $C_{1-3}$alkyl$X^{10}C_{1-3}$alkyl$R^{34}$, (wherein $X^{10}$ is O, S, SO, $SO_2$, $NR^{54}CO$, $ONR^{55}$, $SO_2NR^{56}$, $NR^{57}SO_2$ or $NR^{58}$ (wherein $R^{54}$, $R^{55}$, $R^{56}$, $R^{57}$ and $R^{58}$ each independently are hydrogen, $C_{1-3}$alkyl or $C_{1-3}$alkoxy$C_{2-3}$alkyl) and $R^{34}$ is as defined hereinbefore);

16) $R^{33}$, (wherein $R^{33}$ is as defined hereinbefore); and

17) $C_{1-3}$alkyl$X^{10}C_{1-3}$alkyl$R^{33}$, (wherein $X^{10}$ and $R^{33}$ are as defined hereinbefore)); and wherein n is 1, 2, 3 or 4; and m is 0, 1, 2, 3 or 4; or n is 0, 1, 2, 3 or 4 and m is 1, 2, 3 or 4 and the compound of Formula I is a free base or a salt thereof.

2. A compound according to claim 1, wherein $R^2$ is $C_{1-3}$alkyl, halogeno, cyano, nitro, carbamoyl, N—$C_{1-4}$alkylcarbamoyl, aminosulfonyl, $C_{1-4}$alkoxycarbonyl or a group $R^4X^1$, wherein $X^1$ is $CONR^5R^6$, (wherein $R^5$ is hydrogen or $C_{1-2}$alkyl and wherein $R^4$ is linked to $R^6$); and n is 0, 1 or 2.

3. A compound according to claim 1, wherein $R^3$ is $R^{10}X^2$, wherein $X^2$ is O; and $R^{10}$ is selected from the group consisting of one of the following groups:

1) hydrogen or $C_{1-5}$alkyl;

3) $C_{1-5}$alkyl$X^4R^{21}$, (wherein $X^4$ is O or $NR^{26}$ (wherein $R^{21}$ and $R^{26}$ each independently are hydrogen, $C_{1-3}$alkyl, cyclopentyl or cyclohexyl));

4) $C_{1-5}$alkyl$X^5C_{1-5}$alkyl$X^6R^{27}$, (wherein $X^5$ and $X^6$ are O and $R^{27}$ is hydrogen or $C_{1-3}$alkyl);

5) $C_{1-5}$alkyl$R^{33}$, (wherein $R^{33}$ is a 5 or 6 membered saturated heterocyclic group with one or two heteroatoms selected independently from O, S and N);

9) $C_{1-5}$alkyl$R^{34}$, (wherein $R^{34}$ is a 5 or 6 membered aromatic heterocyclic group with 1 to 3 heteroatoms selected independently from O, N and S, which heterocyclic group may carry up to 5 substituents selected independently from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, hydoxy, cyano, $CONR^{35}R^{36}$ and $NR^{37}COR^{38}$ (wherein $R^{35}$, $R^{36}$, $R^{37}$ and $R^{38}$ each independently are hydrogen, $C_{1-4}$alkyl or $C_{1-3}$alkoxy$C_{2-3}$alkyl));

17) $C_{1-3}$alkyl$X^{10}C_{1-3}$alkyl$R^{33}$, (wherein $X^{10}$ is O and $R^{33}$ is a 5 or 6 membered saturated heterocyclic group with one or two heteroatoms selected independently from O, S and N); and m is 0, 1 or 2.

4. A compound which is selected from the group consisting of 3-[6-(2-Methoxyethoxy)isoquinolin-1-yl]-2-oxo-2,3-dihydro-1H-indole-5-carbonitrile, 3-{6-[2-(2-Methoxyethoxy)ethoxy]isoquinolin-1-yl}-2-oxo-2,3-dihydro-1H-indole-5-carbonitrile, and 3-{6-[2-(2-Methoxyethoxy)ethoxy]isoquinolin-1-yl}-2-oxo-2,3-dihydro-1H-indole-5-carbonitrile trifluoroacetate as a free base or a slat thereof.

5. A pharmaceutical composition comprising as active ingredient a therapeutically effective amount of the compound according to claim 1 in association with pharmaceutically acceptable carriers or diluents.

6. A process for the preparation of the compound of formula I according to claim 1, comprising:

reacting a compound of formula VI, wherein $L^2$ is a leaving group and wherein P, Y, $R^3$ and n are as defined in general formula I, with a compound of formula VII, wherein $R^1$, $R^2$ and m are as defined in general formula I,

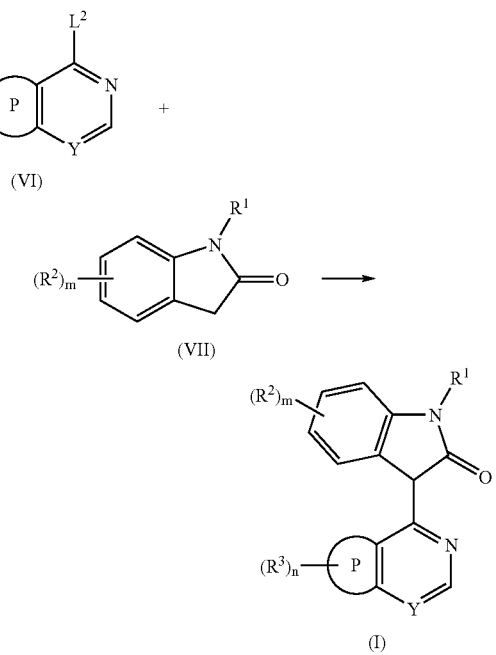

in an appropriate solvent at a temperature in the range of about +10 to about +150° C., optionally in the presence of a base.

7. The process according to claim 6, wherein the compound of formula VI has the following structure

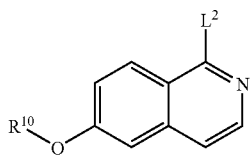

wherein:

$L^2$ is halogeno;

$R^{10}$ is selected from one of the following groups:

1) hydrogen or $C_{1-5}$alkyl which may be substituted with one or more groups selected independently from hydroxy, fluoro and amino;
2) $C_{1-5}$alkyl$X^3$COR$^{16}$, (wherein $X^3$ is O or NR$^{17}$ (wherein R$^{17}$ is hydrogen, $C_{1-3}$alkyl or $C_{1-3}$alkoxy$C_{2-3}$alkyl) and R$^{16}$ is $C_{1-3}$alkyl, NR$^{18}$R$^{19}$ or OR$^{20}$ (wherein R$^{18}$, R$^{19}$ and R$^{20}$ each independently are hydrogen, $C_{1-3}$alkyl or $C_{1-3}$alkoxy$C_{2-3}$alkyl));
3) $C_{1-5}$alkyl$X^4$R$^{21}$, (wherein $X^4$ is O, S, SO, SO$_2$, OCO, NR$^{22}$CO, CONR$^{23}$, SO$_2$NR$^{24}$, NR$^{25}$SO$_2$ or NR$^{26}$ (wherein R$^{22}$, R$^{23}$, R$^{24}$, R$^{25}$ and R$^{26}$ each independently are hydrogen, $C_{1-3}$alkyl or $C_{1-3}$alkoxy$C_{2-3}$alkyl) and R$^{21}$ is hydrogen, $C_{1-3}$alkyl, cyclopentyl, cyclohexyl or a 5 or 6 membered saturated heterocyclic group with one or two heteroatoms selected independently from O, S and N, which $C_{1-3}$alkyl group may be substituted with one or two substituents selected independently from oxo, hydroxy, halogeno and $C_{1-4}$alkoxy and which heterocyclic group may be substituted with one or two substituents selected independently from oxo, hydroxy, halogeno, $C_{1-4}$alkyl, $C_{1-4}$hydroxyalkyl and $C_{1-4}$alkoxy);
4) $C_{1-5}$alkyl$X^5C_{1-5}$alkyl$X^6$R$^{27}$, (wherein $X^5$ and $X^6$ each independently are O, S, SO, SO$_2$, NR$^{28}$CO, CONR$^{29}$, SO$_2$NR$^{30}$, NR$^{31}$SO$_2$ or NR$^{32}$ (wherein R$^{28}$, R$^{29}$, R$^{30}$, R$^{31}$ and R$^{32}$ each independently are hydrogen, $C_{1-3}$alkyl or $C_{1-3}$alkoxy$C_{2-3}$alkyl) and R$^{27}$ is hydrogen or $C_{1-3}$alkyl);
5) $C_{1-5}$alkylR$^{33}$, (wherein R$^{33}$ is a 5 or 6 membered saturated heterocyclic group with one or two heteroatoms selected independently from O, S and N, which heterocyclic group may be substituted with one or two substituents selected independently from oxo, hydroxy, halogeno, $C_{1-4}$alkyl, $C_{1-4}$hydroxyalkyl and $C_{1-4}$alkoxy);
6) $C_{2-5}$alkenylR$^{33}$, (wherein R$^{33}$ is as defined hereinbefore);
7) $C_{2-5}$alkynylR$^{33}$, (wherein R$^{33}$ is as defined hereinbefore);
8) R$^{34}$, (wherein R$^{34}$ is a pyridone group, a phenyl group or a 5 or 6 membered aromatic heterocyclic group with 1 to 3 heteroatoms selected independently from O, N and S, which pyridone, phenyl or heterocyclic group may carry up to 5 substituents selected independently from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, CONR$^{35}$R$^{36}$ and NR$^{37}$COR$^{38}$ (wherein R$^{35}$, R$^{36}$, R$^{37}$ and R$^{38}$ each independently are hydrogen, $C_{1-4}$alkyl or $C_{1-3}$alkoxy$C_{2-3}$alkyl));
9) $C_{1-5}$alkylR$^{34}$, (wherein R$^{34}$ is as defined hereinbefore);
10) $C_{2-5}$alkenylR$^{34}$, (wherein R$^{34}$ is as defined hereinbefore);
11) $C_{2-5}$alkynylR$^{34}$, (wherein R$^{34}$ is as defined hereinbefore);
12) $C_{1-5}$alkyl$X^7$R$^{34}$, (wherein $X^7$ is O, S, SO, SO$_2$, NR$^{39}$CO, CONR$^{40}$, SO$_2$NR$^{41}$, NR$^{42}$SO$_2$ or NR$^{43}$ (wherein R$^{39}$, R$^{40}$, R$^{41}$, R$^{42}$ and R$^{43}$ each independently are hydrogen, $C_{1-3}$alkyl or $C_{1-3}$alkoxy$C_{2-3}$alkyl) and R$^{34}$ is as defined hereinbefore);
13) $C_{2-5}$alkenyl$X^8$R$^{34}$, (wherein $X^8$ is O, S, SO, SO$_2$, NR$^{44}$CO, CONR$^{45}$, SO$_2$NR$^{46}$, NR$^{47}$SO$_2$ or NR$^{48}$ (wherein R$^{44}$, R$^{45}$, R$^{46}$, R$^{47}$ and R$^{48}$ each independently are hydrogen, $C_{1-3}$alkyl or $C_{1-3}$alkoxy$C_{2-3}$alkyl) and R$^{34}$ is as defined hereinbefore);
14) $C_{2-5}$alkynyl$X^9$R$^{34}$ (wherein $X^9$ is O, S, SO, SO$_2$, NR$^{49}$CO, CONR$^{50}$, SO$_2$NR$^{51}$, NR$^{52}$SO$_2$ or NR$^{53}$ (wherein R$^{49}$, R$^{50}$, R$^{51}$, R$^{52}$ and R$^{53}$ each independently are hydrogen, $C_{1-3}$alkyl or $C_{1-3}$alkoxy$C_{2-3}$alkyl) and R$^{34}$ is as defined hereinbefore);
15) $C_{1-3}$alkyl$X^{10}C_{1-3}$alkylR$^{34}$, (wherein $X^{10}$ is O, S, SO, SO$_2$, NR$^{54}$CO, ONR$^{55}$, SO$_2$NR$^{56}$, NR$^{57}$SO$_2$ or NR$^{58}$ (wherein R$^{54}$, R$^{55}$, R$^{56}$, R$^{57}$ and R$^{58}$ each independently are hydrogen, $C_{1-3}$alkyl or $C_{1-3}$alkoxy$C_{2-3}$alkyl) and R$^{34}$ is as defined hereinbefore);
16) R$^{33}$, (wherein R$^{33}$ is as defined hereinbefore); and
17) $C_{1-3}$alkyl$X^{10}C_{1-3}$alkylR$^{33}$, (wherein $X^{10}$ and R$^{33}$ are as defined hereinbefore).

8. A method of treating schizophrenia associated with the inhibition of glycogen synthase kinase-3, depression associated with the inhibition of glycogen synthase kinase-3, and dementia related diseases associated with the inhibition of glycogen synthase kinase-3, wherein the dementia related diseases are selected from the group consisting of Frontotemporal Dementia Parkinson's Type, Parkinson Dementia Complex of Gaum, HIV Dementia, vascular dementia, dentia with Lewy bodies, Frontotemporal Dementia, and Dementia Pugilistica comprising administering to a patient in need of such treatment, a therapeutically effective amount of the compound of Formula (I) as defined in claim 1.

* * * * *